(12) United States Patent  (10) Patent No.: US 7,964,742 B2
Nagarajan et al.  (45) Date of Patent: Jun. 21, 2011

(54) PROCESS FOR PREPARATION OF CITALOPRAM AND ENANTIOMERS

(75) Inventors: Periyandi Nagarajan, Baroda (IN); Kilaru Srinivasu, Baroda (IN); Thennati Rajamannar, Baroda (IN)

(73) Assignee: Sun Pharma Global FZE, Sharjah (AE)

( * ) Notice: Subject to any disclaimer, the term of this patent is extended or adjusted under 35 U.S.C. 154(b) by 0 days.

(21) Appl. No.: 12/813,256

(22) Filed: Jun. 10, 2010

(65) Prior Publication Data

US 2010/0249437 A1  Sep. 30, 2010

Related U.S. Application Data

(62) Division of application No. 11/660,742, filed as application No. PCT/IN2005/000276 on Aug. 12, 2005, now Pat. No. 7,790,935.

(30) Foreign Application Priority Data

Aug. 23, 2004 (IN) ............... 912/MUM/2004

(51) Int. Cl.
*C07D 307/84* (2006.01)
(52) U.S. Cl. .................................... 549/467
(58) Field of Classification Search .............. 549/467
See application file for complete search history.

(56) References Cited

U.S. PATENT DOCUMENTS

| | | | |
|---|---|---|---|
| 4,136,193 A | 1/1979 | Bøgesø et al. | |
| 4,650,884 A | 3/1987 | Bogeso | |
| RE34,712 E | 8/1994 | Boegesoe et al. | |
| 7,112,686 B2 | 9/2006 | Humble et al. | |
| 2005/0065207 A1 | 3/2005 | Sommer et al. | |

FOREIGN PATENT DOCUMENTS

| | | |
|---|---|---|
| WO | 03/051861 A1 | 6/2003 |
| WO | 2005/047274 A1 | 5/2005 |

*Primary Examiner* — Taofiq A Solola
(74) *Attorney, Agent, or Firm* — Sughrue Mion, PLLC

(57) ABSTRACT

The present invention provides a process for preparation of 1-[3-(dimethylamino)propyl]-1-(4-fluorophenyl)-1,3-dihydro-5-isobenzofuran carbonitrile comprising reacting a compound of formula IVa, in the presence of a base with a compound of formula RX,

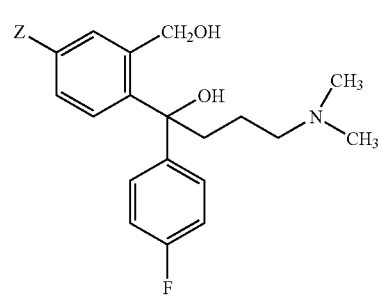

Formula IVa wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl, Z is a cyano group or a group that may be converted to a cyano group;

further wherein RX is selected such that an intermediate ether derivative, a compound of formula Va formed from said reaction cyclizes to a compound of formula VI,

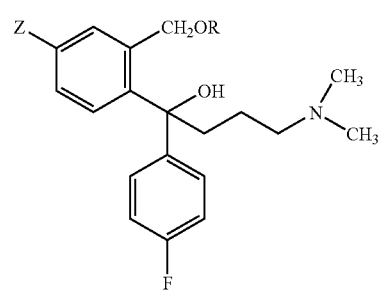

Formula Va

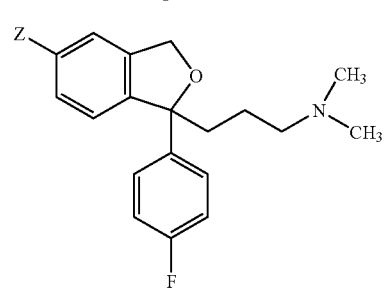

Formula VI and where Z is not a cyano group, conversion of the group Z in the compound of formula VI to a cyano group to form 1-[3-(dimethylamino)propyl]-1-(4-fluorophenyl)-1,3-dihydro-5-isobenzofuran carbonitrile. The present invention also provides novel ether compound, a compound of formula Va and a process for preparation thereof.

6 Claims, No Drawings

PROCESS FOR PREPARATION OF CITALOPRAM AND ENANTIOMERS

This is a Divisional of U.S. patent application Ser. No. 11/660,742, filed Feb. 22, 2007, which is a National Stage Application filed under §371 of PCT Application No. PCT/IN2005/000276 filed Aug. 12, 2005, which claims priority to IN 912/MUM/2004 filed on Aug. 23, 2004. The entire disclosures of the prior applications are considered part of the disclosure of the accompanying divisional application, and are hereby incorporated by reference.

The invention provides a process for preparation of (RS)-(±)-1-[3-(di-methylamino)propyl]-1-(4-fluorophenyl)-1,3-dihydro-5-isobenzofuran bonitrile (a compound of formula I, INN name for the compound is citalopram) and its enantiomers viz., (S)-(+)-1-[3-(dimethylamino)propyl]-1-(4-fluorophenyl)-1,3-dihydro-5-isobenzofuran carbonitrile (a compound of formula II, known as (S)-(+)-citalopram or escitalopram) and (R)-(−)-1-[3-(dimethylamino)propyl]-1-(4-fluorophenyl)-1,3-dihydro-5-isobenzofuran carbonitrile (a compound of formula III) and acid addition salts thereof.

More particularly, the invention provides a process for preparation of citalopram or its enantiomers via novel ether intermediate compounds.

Citalopram was first disclosed in U.S. Pat. No. 4,136,193 and (S)-(+)-citalopram in U.S. RE 34712 (the '712 patent).

U.S. Pat. No. 4,650,884 teaches use of the diol, viz., 4-[4-(dimethylamino)-1-(4-fluorophenyl)-1-hydroxy-1-butyl]-3-(hydroxyl-methyl)-benzonitrile, a compound of formula IV in racemic form, which is cyclized in presence of $H_2SO_4$ to obtain citalopram (Scheme I).

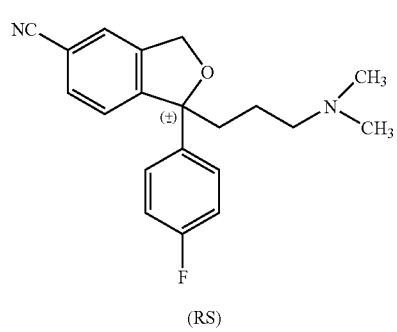

The '712 patent teaches preparation of (S)-(+)-citalopram, a compound of formula II by using the enantiomeric diol compound of formula IV, viz., (S)-(−)-4-[4-(dimethylamino)-1-(4-fluorophenyl)-1-hydroxy-1-butyl]-3-(hydroxymethyl)-benzonitrile, which is derivatized to obtain a labile ester thereof like methanesulfonyl, p-toluenesulfonyl, 10-camphorsulfonyl, trifluoroacetyl or trifluoromethanesulfonyl. The labile ester derivative is cyclized stereoselectively, in presence of a base to obtain the (+)-isomer, namely (S)-(+)-citalopram (Scheme II).

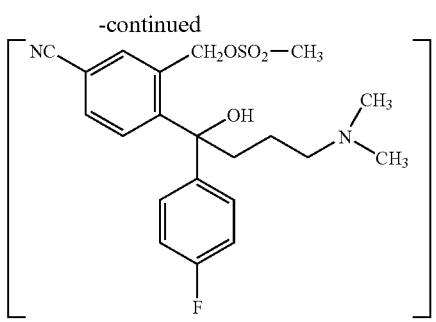

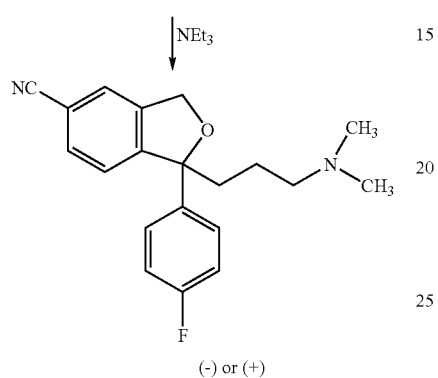

(-) or (+)

The prior art strategies are based on cyclization of the diol under acidic conditions to obtain citalopram or derivatization through a labile ester derivative and cyclization in presence of a base to obtain (S)-(+)-citalopram. These processes of prior art have following disadvantages when the process is to be scaled-up for industrial use:

1. Cyclization of the diol at higher temperature using acids generates amide, acid, indene by-products leading to formation of impure product.
2. Use of the labile esters demonstrated for making enantiomers of citalopram requires use of a reactive agents like methanesulfonyl chloride which could give rise bis-mesylates and thus could lead to the formation of undesired impurities.
3. For preparation of the labile esters, organic bases like triethylamine, pyridine are used as proton scavengers, the undesired labile esters of tertiary alcohol group formed under the reaction condition can proceed via non-concerted manner resulting in chirality perturbation and impurity formation. The excess of base employed can also participate in displacing the reactive ester to form the corresponding ammonium derivatives due to its inherent nucleophilicity.
4. The labile ester is sensitive to moisture, temperature, resulting in decomposition.

There is a need for a convenient, robust process for efficient preparation of citalopram and enantiomers thereof. The present invention provides such a process for preparation of citalopram and enantiomers thereof by use of the racemic or enantiomeric diol intermediate, which is derivatized to obtain an ether derivative thereof, which can be cyclised in-situ to obtain citalopram or enantiomers thereof. The ether derivatives are formed at the primary alcohol group of the diol intermediate by reacting with aryls, heteroaryls or alkyls optionally substituted with electron withdrawing groups.

The present invention provides a process for preparation of citalopram or enantiomers thereof, particularly, (S)-(+)-citalopram of desired enantiomeric purity.

SUMMARY OF THE PRESENT INVENTION

The present invention provides a process for preparation of 1-[3-(dimethylamino)propyl]-1-(4-fluorophenyl)-1,3-dihydro-5-isobenzofuran carbonitrile comprising reacting a compound of formula IVa, in the presence of a base with a compound of formula RX,

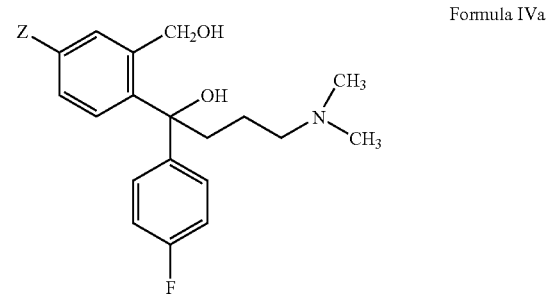

Formula IVa wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl, Z is a cyano group or a group that may be converted to a cyano group; further wherein RX is selected such that an intermediate ether derivative, a compound of formula Va formed from said reaction cyclizes to a compound of formula VI,

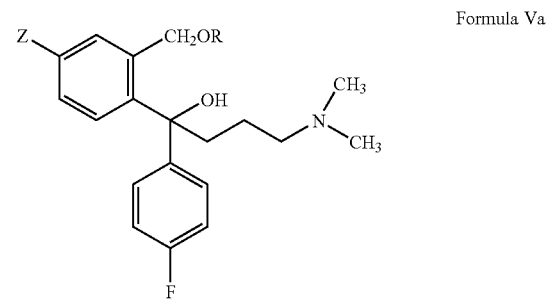

Formula Va

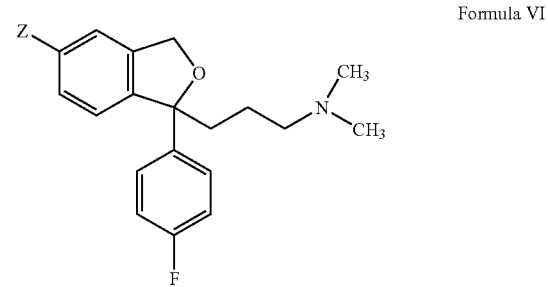

Formula VI and where Z is not a cyano group, conversion of the group Z in the compound of formula VI to a cyano group to form 1-[3-(dimethylamino)propyl]-1-(4-fluorophenyl)-1,3-dihydro-5-isobenzofuran carbonitrile.

The present invention in one embodiment provides a process for preparation of 1-[3-(dimethylamino)propyl]-1-(4-fluorophenyl)-1,3-dihydro-5-isobenzofuran carbonitrile comprising reacting 4-[4-(dimethylamino)-1-(4-fluorophenyl)-1-hydroxy-1-butyl]-3-(hydroxymethyl)-benzonitrile, in the presence of a base, with a compound of formula RX, wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl; further wherein RX is selected such that an intermediate ether derivative, a compound of formula V formed from said reaction,

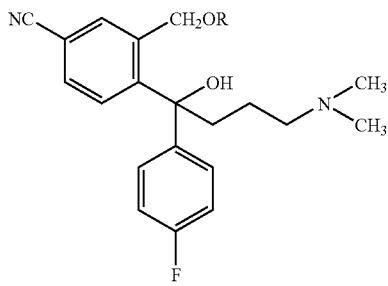

Formula V cyclizes to 1-[3-(dimethylamino)propyl]-1-(4-fluorophenyl)-1,3-dihydro-5-isobenzofuran carbonitrile.

The present invention provides novel ether compound, a compound of formula Va, or acid addition salt thereof,

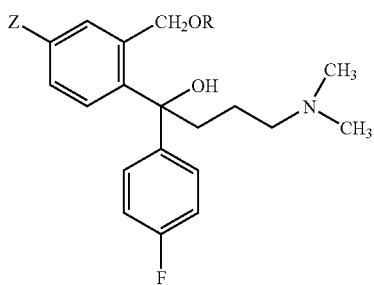

Formula Va wherein R is selected from alkyl, alkenyl, aryl and heteroaryl which may be optionally substituted with electron withdrawing groups and Z is a cyano group or a group that may be converted to a cyano group.

The present invention in one embodiment provides novel ether compound, a compound of formula V or acid addition salt thereof,

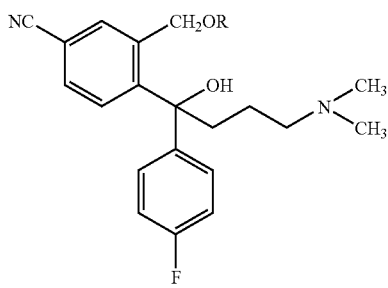

Formula V wherein R is selected from alkyl, alkenyl, aryl and heteroaryl which may be optionally substituted with electron withdrawing groups.

The present invention provides a process for preparation of a compound of formula Va, comprising reacting a compound of formula IVa, in the presence of a base with a compound of formula RX,

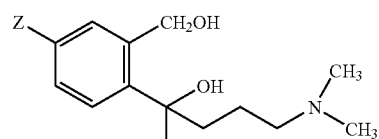

Formula IVa

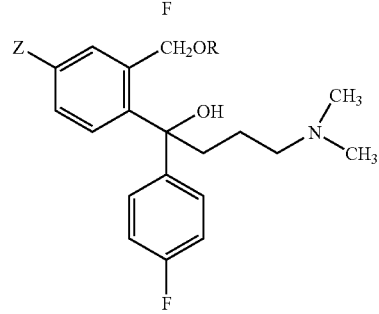

Formula Va wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl, Z is a cyano group or a group that may be converted to a cyano group.

The present invention in one embodiment provides a process for preparation of a compound of formula V,

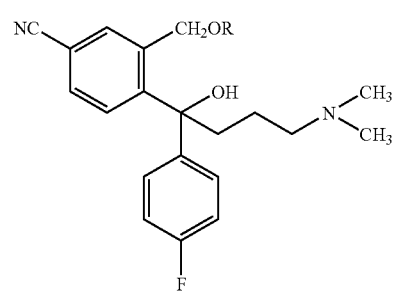

Formula V comprising reacting 4-[4-(dimethylamino)-1-(4-fluorophenyl)-1-hydroxy-1-butyl]-3-(hydroxymethyl)-benzonitrile, in the presence of a base, with a compound of formula RX, wherein R is selected from alkyl, alkenyl, aryl and heteroaryl which may be optionally substituted with electron withdrawing groups and X is selected from F, Cl, Br, I, CN, OTf and OR1, wherein Tf represents trifluoromethanesulfonyl group, and R1 is optionally substituted alkyl.

DETAILS OF THE PRESENT INVENTION

As used herein 1-[3-(dimethylamino)propyl]-1-(4-fluorophenyl)-1,3-dihydro-5-isobenzofuran carbonitrile may represent a racemic or an enantiomeric compound, especially (S)-(+)-isomer thereof, unless otherwise specified.

The compound of formula IVa, the compound of formula Va or the compound of formula VI represents a racemic or an enantiomeric compound, unless otherwise specified.

Z is a cyano group or a group that may be converted to a cyano group. Such groups, Z, may be selected from halogen, —OH, —CHO, —CH$_2$OH, —CH$_2$NH$_2$, —CH$_2$NO$_2$, —CH$_3$, —CH$_2$Cl, —CH$_2$Br, —NHR$_2$, —COOR$_S$, —CONR$_3$R$_4$, CF$_3$—(CF$_2$)$_n$—SO$_2$—O— wherein n is 0-8, R$_2$ is hydrogen or C1 to C6 alkylcarbonyl and R$_2$ and R$_3$ are selected from hydrogen, optionally substituted C1 to C6 alkyl or aryl and, a group of formula VII:

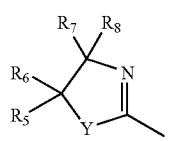

Formula VII wherein Y is O or S; R$_5$ and R$_6$ are each independently selected from hydrogen and C1 to C6 alkyl or R$_5$ and R$_6$ together form a C2 to C5 alkylene chain thereby forming a spiro ring; R$_7$ is selected from hydrogen, C1 to C6 alkyl, R$_9$ is selected from hydrogen, C1 to C6 alkyl, a carboxy group or a precursor group thereof, or R$_7$ and R$_8$ together form a C2 to C5 alkylene chain thereby forming a spiro ring.

When Z is halogen, in particular bromo or chloro, conversion of the compound of formula VI to form 1-[3-(dimethylamino)propyl]-1-(4-fluorophenyl)-1,3-dihydro-5-isobenzofuran carbonitrile may be carried out by any process as known in the art, for example as described in U.S. Pat. No. 4,136,193, PCT publications WO 00/13648, WO 00/11926 or WO 01/02383.

Compounds of formula VI, wherein the group Z is CF$_3$—(CF$_2$)$_n$—SO$_2$—O—, wherein n is 0-8, may be converted to 1-[3-(dimethylamino)propyl]-1-(4-fluorophenyl)-1,3-dihydro-5-isobenzofuran carbonitrile by methods analogous to those described in PCT publication WO 00/13648.

Compounds of formula VI, wherein the group Z is —CHO, may be converted to 1-[3-(dimethylamino)propyl]-1-(4-fluorophenyl)-1,3-dihydro-5-isobenzofuran carbonitrile by methods analogous to those described in PCT publication WO 99/30548.

Compounds of formula VI, wherein the group Z is —NHR$_2$, wherein R$_2$ is hydrogen or alkylcarbonyl, may be converted by to 1-[3-(dimethylamino)propyl]-1-(4-fluorophenyl)-1,3-dihydro-5-isobenzofuran carbonitrile by methods analogous to those described in PCT publication WO 98/19512.

Compounds of formula VI, wherein the group Z is —COOR$_3$ or —CONR$_3$R$_4$, wherein R$_3$ and R$_4$ are selected from hydrogen and optionally substituted alkyl or aryl may be converted to 1-[3-(dimethylamino)propyl]-1-(4-fluorophenyl)-1,3-dihydro-5-isobenzofuran carbonitrile by methods analogous to those described in PCT publications WO 98/19511 and WO 98/19513.

Compounds of formula VI, wherein the group Z is a group of formula VII may be converted to 1-[3-(dimethylamino)propyl]-1-(4-fluorophenyl)-1,3-dihydro-5-isobenzofuran carbonitrile by methods analogous to those described in PCT publication WO 00/23431.

Compounds of formula VI, wherein Z is OH, —CH$_2$OH, —CH$_2$NH$_2$, —CH$_2$NO$_2$, —CH$_2$Cl, —CH$_2$Br, —CH$_3$ or any of the groups above, may be converted to 1-[3-(dimethylamino)propyl]-1-(4-fluorophenyl)-1,3-dihydro-5-isobenzofuran carbonitrile by methods analogous to those described in PCT publications WO 01/68632 and WO 01/85712.

Starting materials of formula IVa may be prepared according to the above mentioned patents and patent applications, which are incorporated herein by reference or by analogous methods known in the art.

The compound RX is a compound, which can react with a compound of formula IVa such as, 4-[4-(dimethylamino)-1-(4-fluorophenyl)-1-hydroxy-1-butyl]-3-(hydroxymethyl)-benzonitrile to form a ether derivative, a compound of formula Va, via addition-elimination type reaction, X being any suitable leaving group. A suitable leaving group is any group which upon reaction of a compound of formula IVa with the compound RX, facilitates formation of an ether derivative represented by a compound of formula Va.

In a preferred embodiment RX is a compound of formula, wherein R is selected from alkyl, alkenyl, aryl and heteroaryl which may be optionally substituted with electron withdrawing groups and X is selected from F, Cl, Br, I, CN, OTf and OR$_1$, wherein Tf represents trifluoromethanesulfonyl group, and R$_1$ is alkyl optionally substituted with electron withdrawing groups.

RX is further selected from compounds capable of forming an ether derivative, a compound of formula Va.

In the process of the invention, a compound of formula Va is formed by reaction of compound of formula IVa with a compound of formula RX, in presence of a base. The compound of formula Va can in-situ cyclize to form a compound of formula VI. If desired it can be isolated and then subjected to cyclization in presence of a base.

In a preferred embodiment, the ether derivative compound of formula V, formed by reaction of 4-[4-(dimethylamino)-1-(4-fluorophenyl)-1-hydroxy-1-butyl]-3-(hydroxymethyl)-benzonitrile with a compound of formula RX, in presence of a base, cyclizes in-situ to directly form 1-[3-(dimethylamino)propyl]-1-(4-fluorophenyl)-1,3-dihydro-5-isobenzofuran carbonitrile. However, if it is so desired, the ether derivative compound of formula V may be isolated and subjected to cyclization in presence of a base.

Further, preferably, the compound RX is not labile like methanesulfonyl chloride used in the prior art, the '712 patent, and thus resulting in an advantage of easier handling and storage and leading to preparation of chirally pure S-(+)-citalopram end product. The use of methanesulfonyl chloride may give rise to bismesylates leading to formation of undesired impurities with chirality perturbation.

The present invention provides novel ether compound, a compound of formula Va, or acid addition salt thereof,

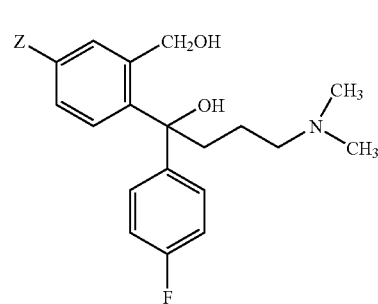

Formula IVa

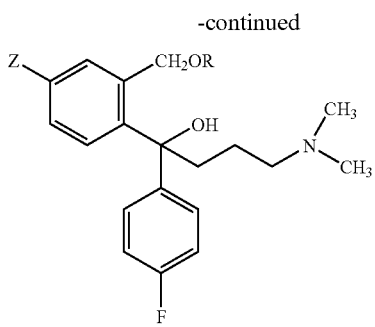

Formula Va and a process for preparation thereof comprising reacting a compound of formula IVa, in the presence of a base, with a compound of formula RX, wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl, Z is a cyano group or a group that may be converted to a cyano group.

The present invention in one embodiment provides novel ether compound, a compound of formula V, or acid addition salt thereof,

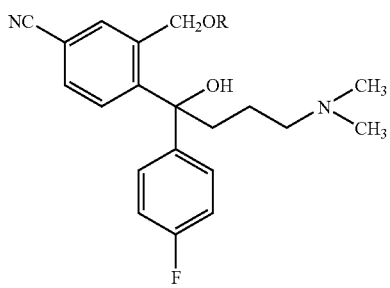

Formula V and a process for preparation thereof comprising reacting 4-[4-(dimethylamino)-1-(4-fluorophenyl)-1-hydroxy-1-butyl]-3-(hydroxyl-methyl)-benzonitrile, in the presence of a base, with a compound of formula RX, wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl.

In a preferred embodiment, the present invention provides 4-[4-(dimethylamino)-1-(4-fluorophenyl)-1-hydroxy-1-butyl]-3-(2-nitro-4-chlorophenoxymethyl)-benzonitrile, a compound of formula VIII, or acid addition salt thereof,

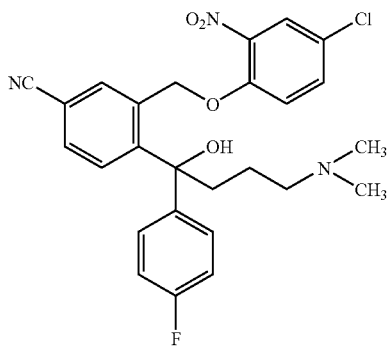

Formula VIII and a process for preparation thereof comprising reacting 4-[4-(dimethylamino)-1-(4-fluorophenyl)-1-hydroxy-1-butyl]-3-(hydroxyl-methyl)-benzonitrile, in the presence of a base, with 2,5-dichloronitrobenzene.

In a more preferred embodiment, the present invention provides novel (S)-4-[4-(dimethylamino)-1-(4-fluorophenyl)-1-hydroxy-1-butyl]-3-(2-nitro-4-chlorophenoxy-methyl)-benzonitrile or an acid addition salt thereof for example, hydrochloride salt.

In a particularly preferred embodiment, the present invention provides (S)-(−)-4-[4-(dimethylamino)-1-(4-fluorophenyl)-1-hydroxy-1-butyl]-3-(2-nitro-4-chlorophenoxy-methyl)-benzonitrile hydrochloride.

The acid addition salt of compound of formula V, Va or VIII may be prepared by any standard method of contacting the compound of formula V, Va or VIII with an acid, for example inorganic acid like hydrochloric acid, hydrobromic acid, sulfuric acid, nitric acid, phosphoric acid and the like or organic acid like oxalic acid, citric acid, succinic acid, cinnamic acid, p-toluenesulfonic acid and the like.

As used herein, "alkyl" may be any straight, branched, or cyclic alkyl group of C1 to C6 atoms, optionally substituted with one or more electron withdrawing groups selected from nitro, halo, cyano, 4-trifluoroalkyl, 2,4-bis(trifluoroalkyl), 2,6-bis(trifluoroalkyl), —CHO, —$COOR_9$, wherein $R_9$ may be alkyl, aryl or heteroaryl.

As used herein, "alkenyl" may be any straight, branched, or cyclic alkyl group of C1 to C6 atoms, optionally substituted with one or more electron withdrawing groups selected from nitro, halo, cyano, 4-trifluoroalkyl, 2,4-bis(trifluoroalkyl), 2,6-bis(trifluoroalkyl), —CHO, —$COOR_9$, wherein $R_9$ may be alkyl, aryl or heteroaryl.

As used herein, "aryl" may be a mono-, bi- or polycyclic aromatic system, for example phenyl, naphthyl, optionally substituted with one or more electron withdrawing groups selected from nitro, halo, cyano, 4-trifluoroalkyl, 2,4-bis(trifluoroalkyl) or 2,6-bis(trifluoroalkyl), —CHO, —$COOR_9$, wherein $R_9$ may be alkyl, aryl or heteroaryl.

As used herein, "heteroaryl" may be a mono-, bi- or polycyclic aromatic system containing one or more hetero atom which may be same or different, for example quinolinyl, isoquinolinyl, pyridinyl, indanyl, fluorenyl, oxazolyl, pyrazinyl, thienyl, quinazolinyl, benzimidazolyl and the like optionally substituted with one or more electron withdrawing groups selected from nitro, halo, cyano, 4-trifluoroalkyl, 2,4-bis(trifluoroalkyl) or 2,6-bis(trifluoroalkyl), —CHO, —$COOR_9$, wherein $R_9$ may be alkyl, aryl or heteroaryl.

As used herein, "hetero atom" may preferably be selected from N, O, S or P.

The base used may be selected from an alkoxide, wherein the alkyl residue is C1 to C6 linear, branched or cyclic alkyl and the counter ion is an alkali or alkaline earth metal; alkali or alkaline earth metal oxide, hydroxide, carbonate or bicarbonate or an amine base. The amine base may be selected from aliphatic or aromatic amines, cyclic or acyclic amines, for example isoquinolines, quinolines, dialkylarylamines, pyridine, substituted pyridines. The base may be selected from moderate bases that do not favor the formation of bis-alkoxides thus providing control over the derivatization of the primary alcohol group of the diol.

The ether derivative compounds represented by a compound of formula V or Va can cyclize to form citalopram or enantiomers thereof. When the diol compound, viz., a compound of formula IV or IVa is used in enantiomeric form, derivatized to form an ether derivative thereof, a compound of formula V or Va, it cyclizes stereoselectively to afford enantiomerically pure citalopram.

In a preferred embodiment, the group R is:

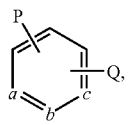

wherein one or more of a, b and c may be carbon or hetero atom which may be same or different, P and Q may be selected from electron withdrawing groups like $NO_2$, $CF_3$, CN, halogen, $COOR_S$, CHO and the like, wherein $R_9$ is alkyl, aryl or heteroaryl.

In another preferred embodiment the compound of formula RX is selected from the group consisting of the following compounds:

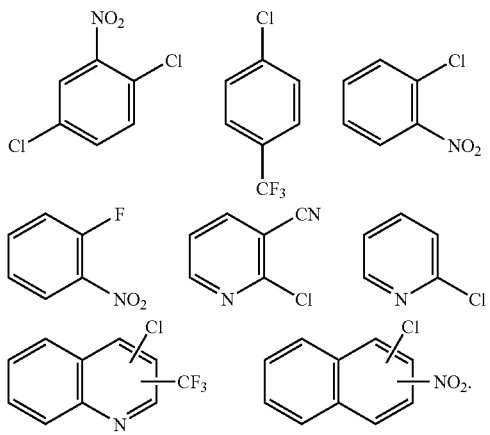

In one embodiment the present invention provides a process for preparation of racemic 1-[3-(dimethylamino)propyl]-1-(4-fluorophenyl)-1,3-dihydro-5-isobenzofuran carbonitrile comprising reacting racemic 4-[4-(dimethylamino)-1-(4-fluorophenyl)-1-hydroxy-1-butyl]-3-(hydroxymethyl)-benzonitrile, with a compound of formula RX, in presence of a base. Preferably the compound of formula RX is dichloronitrobenzene.

In another embodiment the present invention provides a process for preparation of enantiomeric 1-[3-(dimethylamino)propyl]-1-(4-fluorophenyl)-1,3-dihydro-5-isobenzofuran carbonitrile comprising reacting enantiomeric 4-[4-(dimethylamino)-1-(4-fluorophenyl)-1-hydroxy-1-butyl]-3-(hydroxymethyl)-benzonitrile, with a compound of formula RX, in presence of a base. Preferably the compound of formula RX is dichloronitrobenzene.

In another preferred embodiment the present invention provides a process for preparation of (S)-(+)-1-[3-(dimethylamino)propyl]-1-(4-fluorophenyl)-1,3-dihydro-5-isobenzofuran carbonitrile comprising reacting (S)-(−)-4-[4-(dimethylamino)-1-(4-fluorophenyl)-1-hydroxy-1-butyl]-3-(hydroxylmethyl)-benzonitrile, with a compound of formula RX, in presence of a base. Preferably the compound of formula RX is dichloronitrobenzene.

In a particularly preferred embodiment the present invention provides a process for preparation of (S)-(+)-1-[3-(dimethylamino)propyl]-1-(4-fluorophenyl)-1,3-dihydro-5-isobenzofuran carbonitrile comprising reacting (S)-(−)-4-[4-(dimethylamino)-1-(4-fluorophenyl)-1-hydroxy-1-butyl]-3-(hydroxymethyl)-benzonitrile with 2,5-dichloronitrobenzene, in presence of a base to form a compound of formula VIII,

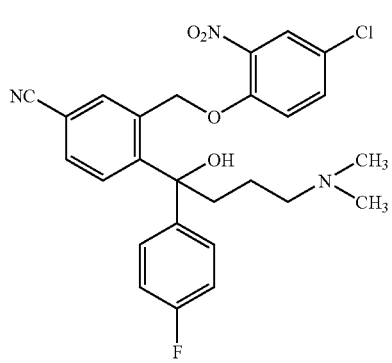

Formula VIII and cyclization of compound of formula VIII.

The process of the present invention may be carried out in any suitable solvent. Examples of solvents that may be used are alcohol solvents like methanol, ethanol, t-butanol, polyethyleneglycol; ketone solvents like acetone, methyl iso-butyl ketone; ether solvents like tetrahydrofuran, dioxane; ester solvents like ethylacetate, butylacetate; amide solvents like dimethylformamide, dimethylacetamide; nitrile solvents like acetonitrile; dipolar aprotic solvents like dimethylsulfoxide, sulfolane; hydrocarbon and aromatic hydrocarbon solvents having a boiling point greater than 70° C.

The process of the present invention can be carried out in a suitable solvent with a base at temperature ranging from ambient to the reflux temperature of the selected solvent. The reaction may be completed in 0.5 to 40 hours, preferably 0.5 to 20 hours depending on the selected solvent and base.

In a typical procedure, the reaction may be worked-up by quenching by addition of 2 to 10 volumes, preferably 3 to 8 volumes of water to the reaction solvent, depending on the product solubility in the selected solvent, at temperature between the range of 0° C. to 100° C., preferably 20° C. to 60° C. The reaction mixture may be extracted with a suitable water-immiscible solvent like toluene, ether, ethylacetate.

If desired, 1-[3-(dimethylamino)propyl]-1-(4-fluorophenyl)-1,3-dihydro-5-isobenzofuran carbonitrile may be converted to a pharmaceutically acceptable acid addition salt thereof by treatment with organic or inorganic acid. Examples of organic acids are oxalic, fumaric, succinic mandelic, benzoic, p-toluenesulfonic acid and the like. Examples of inorganic acids are hydrobromic, hydrochloric, sulfuric, phosphoric, nitric and the like. The preparation of salt formation may be carried out in a solvent like acetone, water, methanol, isopropanol, dimethylformamide or mixture thereof.

The worked out examples given below illustrate the process and not to be construed as limiting.

EXAMPLES

Example 1

Preparation of Citalopram Oxalate

To a solution of 10 gm of (RS)-(±)4-[4-(dimethylamino)-1-(4-fluorophenyl)-1-hydroxy-1-butyl]-3-(hydroxymethyl)-benzonitrile in 50 ml of dimethylsulfoxide (DMSO) at room temperature was added 12 gm of anhydrous $K_2CO_3$ and 6.73 gm of 2,5-dichloronitrobenzene was added to the above reaction mixture at room temperature and stirred at 100° C. for 15 hours. To the reaction mixture, 250 ml of water was added and extracted with toluene, the toluene layer was washed with water and 5% sodium hydroxide solution and after acid base treatment yielded an oily product. The oil was dissolved in 40 ml of acetone at 30° C. and 3.4 gm of oxalic acid dihydrate was added to it, stirred, cooled, filtered and dried at 60° C.

Dry wt: 7.8 gm.

Example 2

Preparation of (S)-(+)-Citalopram Oxalate

To a solution of 6 gm of (S)-(−)-4-[4-(dimethylamino)-1-(4-fluorophenyl)-1-hydroxy-1-butyl]-3-(hydroxymethyl-benzoate)-benzonitrile in 60 ml tetrahydrofuran (THF) was added 4.33 gm of potassium tertiary butoxide at 0-10° C. and stirred for 30 minutes. A solution of 4.04 gm of 2,5-dichloronitrobenzene in 30 ml THF at 0-10° C. was added to it and stirred for 10-15 hours at room temperature, followed by addition of 250 ml of water. The reaction mixture was extracted with toluene, the toluene layer was washed with water and 5% sodium hydroxide solution and after acid base treatment yielded an oily product. The oil was dissolved in 16 ml of acetone at 30° C. and 1.75 gm of oxalic acid dihydrate in 8 ml acetone was added to it, stirred, cooled, filtered and dried at 60° C. to get the oxalic acid salt of (S)-(+)-1-[3-(dimethylamino)propyl]-1-(4-fluorophenyl)-1,3-dihydro-5-isobenzofuran carbonitrile.

Dry wt: 4.3 gm, $[\alpha]_D$=+11.8° (c=1, methanol).
Chiral HPLC: R-isomer content: 0.64%

Example 3

Preparation of (S)-(+)-Citalopram Oxalate

To a solution of 6.0 gm of (S)-(−)-4-[4-(dimethylamino)-1-(4-fluorophenyl)-1-hydroxy-1-butyl]-3-(hydroxymethyl)-benzonitrile in 30 ml of DMSO at room temperature was added 7.3 gm of anhydrous $K_2CO_3$ and 4.04 gm of 2,5-dichloronitrobenzene was added to the above reaction mixture at room temperature and stirred at 100° C. for 15.0 hours. To the above reaction mixture, 120 ml of water was added, and extracted with toluene. The toluene layer was washed with water and 5% sodium hydroxide solution and after acid base treatment yielded an oily product. The oil was dissolved in 16 ml of acetone at 30° C. and 1.9 gm of oxalic acid dihydrate in 8 ml of acetone was added to it, stirred, cooled, filtered and dried at 60° C.

Dry wt: 4.1 gm, $[\alpha]_D$=+12.62° (c=1, methanol).
Chiral HPLC: R-isomer content: 0.2%

Example 4

Preparation of (S)-(+)-Citalopram Oxalate

To a solution of 64 Kg of (S)-(−)-4-[4-(dimethylamino)-1-(4-fluorophenyl)-1-hydroxy-1-butyl]-3-(hydroxymethyl-benzoate)-benzonitrile in 300 lit DMSO was added 77.48 Kg of anhydrous $K_2CO_3$ and 43.06 Kg of 2,5-dichloronitrobenzene at room temperature and stirred for 16 hours at 100-105° C. To the reaction mixture 3000 ml of water was added at about 30° C. The reaction mixture was extracted with toluene, the toluene layer was washed with water and 5% sodium hydroxide solution and after acid base treatment yielded an oily product. The oil was dissolved in 510 lit of isopropanol at about 30° C. and 20.4 lit water added, stirred for 10 minutes and 20.8 Kg of oxalic acid dihydrate was added and heated to about 70-75° C., stirred, charcolised, cooled and filtered. The filtrate was cooled to 5-10° C. slowly and the resultant solid was filtered, dried at 60° C. and micronised to get the oxalic acid salt of (S)-(+)-1-[3-(dimethylamino)propyl]-1-(4-fluorophenyl)-1,3-dihydro-5-isobenzofuran carbonitrile.

Dry wt: 61.5 Kg, $[\alpha]_D$=+13.85° (c=1, methanol).
Chiral HPLC: R-isomer content: 0.38%.
Purity by HPLC: 99.25%.

Example 5

Preparation of S-(−)-4-[4-(dimethylamino)-1-(4-fluorophenyl)-1-hydroxy-1-butyl]-3-(2-nitro-4-chlorophenoxymethyl)-benzonitrile hydrochloride To a solution of 5.6 gm of (S)-(−)-4-[4-(dimethylamino)-1-(4-fluorophenyl)-1-hydroxy-1-butyl]-3-(hydroxymethyl)-benzonitrile in 85 ml THF was added 2.02 gm of potassium tertiary butoxide at 0-10° C. and stirred for 10 min. 3.14 gm of 2,5-dichloronitrobenzene was added to the reaction mixture at 0-10° C. and stirred for 10-15 hrs at RT (30-35° C.), solvent distilled under vacuum and 40 ml of water was added, and extracted with toluene, toluene layer was washed with water and 10% sodium hydroxide solution and distilled to get an oily product, which is purified by column chromatography using silica gel and ethylacetate, Wt: 500 mg.

The above oily product was dissolved in 10 ml of isopropanol (IPA) at 30° C. and 2.0 ml of IPA-HCl was added, stirred and solvent distilled under vacuum and crystallized in IPA to get (−)-4-[4-(dimethylamino)-1-(4-fluorophenyl)-1-hydroxy-1-butyl]-3-(2-nitro-4-chlorophenoxymethyl)-benzonitrile hydrochloride whose structure was confirmed by IR, NMR and Mass spectral data.

Dry wt: 300 mg, $[\alpha]_D$=−46.8° (c=1, methanol).
Analysis calculated for $C_{26}H_{26}N_3O_4Cl_2F$: C, 58.44; H, 4.90; N, 7.86. found: C, 57.42; H, 4.65; N, 7.33.
$^1$HNMR (400.13 MHz, DMSO-d6) δ1.42-1.43 (broad m, 1H); 1.75-1.76 (broad m, 1H); 2.32-2.47 (m, 2H); 2.70 (s, 6H); 3.00-3.13 (m, 2H); 5.03 (d, J=14.01 Hz, 1H); 5.43 (d, J=14.04 Hz, 1H); 6.43 (s, 1H); 6.52 (d, J=9.09 Hz, 1H,); 7.18 (t, J=8.85 Hz, 2H); 7.39 (dd, $J_1$=8.71 Hz, $J_2$=5.41 Hz, 2H); 7.54 (dd, $J_1$=8.97 Hz, $J_2$=2.63 Hz, 1H); 7.90 (s, 1H); 7.96 (d, J=8.25 Hz, 1H); 8.03 (d, J=8.25 Hz, 1H,); 8.08 (d, J=2.63 Hz, 1H); 10.36 (s, 1H).
$^{13}$CNMR (100.61 MHz, DMSO-d6) δ18.44 (t); 38.87 (t); 41.86 (2q); 56.47 (t); 67.83 (t); 76.63 (s); 110.49 (s); 114.84 (2d, J=21.23 Hz); 116.11 (d); 124.93 (d); 118.48 (s); 124.17 (s); 127.57 (d); 127.88 (2d, J=8.02 Hz); 130.99 (d); 131.31 (d); 133.84 (d); 136.47 (s); 139.55 (s); 140.89[s (d, J=2.80 Hz)]; 149.27 (s); 149.45 (s); 160.91[s (d, J=243.67 Hz)].
Mass: CI Mode, $M^+$=498.20 (0.87%); (M-173)=325.30 (100.0%).
IR (KBr): cm$^{-1}$ 735.02, 747.45; 1162.70, 1230.44; 1507.93, 1603.51; 1283.12, 1528.82; 2226.34; 2935.53, 3039.88, 3062.31; 3249.93.

Example 6

Preparation of (S)-(+)-Citalopram

To a solution of 100 mg of (S)-(−)-4-[4-(dimethylamino)-1-(4-fluorophenyl)-1-hydroxy-1-butyl]-3-(2-nitro-4-chlorophenoxymethyl)-benzonitrile hydrochloride in 2.0 ml of DMSO was added 64.5 mg of potassium carbonate at 30-35°

C. and stirred for 30 min at 95-100° C. After reaction completion which is monitored by TLC, 40 ml of water was added, and extracted with toluene, toluene layer was washed with water and 10% sodium hydroxide solution and distilled out toluene to get an oily product.

Wt: 65.0 mg

Chiral HPLC: S-isomer content: 100%.

$^1$HNMR (400.13 MHz, CDCl$_3$) δ1.27-1.38 (m, 1H); 1.41-1.53 (m, 1H); 2.13 (s, 6H); 2.09-2.25 (m, 4H); 5.15 (d, J=12.96 Hz, 1H); 5.19 (d, J=12.96 Hz, 1H); 6.98-7.02 (m, 2H); 7.38-7.49 (m, 4H); 7.58 (d, J=7.77 Hz, 1H).

Example 7

Preparation of (S)-(+)-Citalopram

Given below in Table I is the comparison between (S)-(+)-citalopram oxalate prepared by:

A] the prior art process using the methanesulfonyl ester derivative (Experiments A(1), A(2) and A(3)) and B] the process of the present invention using the ether derivative compound VIII (Experiments B(1), B(2) and B(3)):

TABLE I

| | | | (S)-(+)-citalopram oxalate | | | | |
|---|---|---|---|---|---|---|---|
| | | | Chiral HPLC purity % | | Specific optical | HPLC | |
| Experiment No. | Batch No. | No. of the starting diol | S-isomer | R-isomer | rotation (1% methanol) | Purity % | Unknown impurity % |
| A(1) | 1511-S/F/771/15 | PN 42701 | 98.96 | 1.04 | +13.1° | 99.59 | 0.18 |
| A(2) | 1511-S/F/771/16 | PN 41864 | 99.16 | 0.84 | +13.0° | 99.69 | 0.09 |
| A(3) | 1511-S/F/771/20 | 1511-S/II/771/10A | 99.15 | 0.85 | +12.9° | 98.95 | 0.6 |
| B(1) | 1511-S/F/771/17 | PN 42701 | 99.66 | 0.34 | +13.2° | 99.76 | 0.05 |
| B(2) | 1511-S/F/771/18 | PN 41864 | 99.62 | 0.38 | +13.1° | 99.77 | 0.05 |
| B(3) | 1511-S/F/771/19 | 1511-S/II/771/10A | 99.77 | 0.23 | +13.4° | 99.76 | 0.03 |

Experiment A(1):

To a solution of 16 gm of (S)-(−)-4-[4-(dimethylamino)-1-(4-fluorophenyl)-1-hydroxy-1-butyl]-3-(hydroxymethylbenzoate)-benzonitrile in 128 ml dichloromethane was added 14.2 gm of triethylamine, stirred and cooled and 8.0 gm of methanesulfonylchloride was added at below 10° C. and stirred at less than 10° C. for 1.0 hr. To the reaction mixture 65 ml of water was added and extracted with dichloromethane. The dichloromethane layer was washed with water and distilled and dissolved the material in toluene, the toluene layer was washed with water and distilled to get an oily product. The oil was dissolved in 50 ml acetone and 5.12 gm of oxalic acid dihydrate in 50 ml acetone was added to it at room temperature, stirred and cooled. The filtrate was cooled to 5-10° C. slowly and the resultant oxalate salt was filtered, dried at 60° C. and purified by dissolving in 420 ml acetone, heated to reflux temperature, stirred to get clear solution, charcolized and distilled to a residual volume of 75 ml, cooled to 5-10° C. slowly and the resultant solid was filtered, dried at 60° C. to get the oxalic acid salt of (S)-(+)-1-[3-(dimethylamino)propyl]-1-(4-fluorophenyl)-1,3-dihydro-5-isobenzofuran carbonitrile.

Dry wt: 9.4 gm $[α]_D$=+13.1° (c=1, methanol).

Chiral HPLC: R-isomer content: 1.04%.

Purity by HPLC: 99.59%.

Experiments A(2) and A(3) have been carried out in similar way as in Experiment No. A(1). Comparative Experiments A(1), A(2) and A(3) have been carried out according to the teaching of prior art, U.S. Pat. No. Re 34712, which is incorporated herein by reference.

Experiment B(1):

To a solution of 16 gm of (S)-(−)-4-[4-(dimethylamino)-1-(4-fluorophenyl)-1-hydroxy-1-butyl]-3-(hydroxymethylbenzoate)-benzonitrile in 75 ml DMSO was added 19.3 gm of anhydrous K$_2$CO$_3$ and 10.8 gm of 2,5-dichloronitrobenzene at room temperature and stirred for 15 hours at 100-105° C. To the reaction mixture 750 ml of water was added at about 30° C. The reaction mixture was extracted with toluene, the toluene layer was washed with water and 5% sodium hydroxide solution and after acid base treatment yielded an oily product. The oil was dissolved in a mixture of 125 ml IPA and 5 ml water at 30° C. and 5.3 gm of oxalic acid dihydrate was added to it, heated to 70-75° C., stirred and charcolized to get clear solution, cooled to 5-10° C. slowly and the resultant oxalate salt was filtered, dried at 60° C. and purified by dissolving in a mixture of 140 ml isopropanol and 5.6 ml water at 30° C. heated to 70-75° C., stirred to get a clear solution, cooled to 5-10° C. slowly and the resultant solid was filtered, dried at 60° C. to get the oxalic acid salt of (S)-(+)-1-[3-(dimethylamino)propyl]-1-(4-fluorophenyl)-1,3-dihydro-5-isobenzofuran carbonitrile.

Dry wt: 13.3 gm $[α]_D$=+13.2° (c=1, methanol).

Chiral HPLC: R-isomer content: 0.34%.

Purity by HPLC: 99.76%.

Experiments B(2) and B(3) have been carried out in similar way as in Experiment No. B(1), which illustrate the process of the present invention.

It is evident from the data presented in Table I and the worked out examples, that (S)-(+)-citalopram prepared by the process of the present invention contains R-isomer in the range of 0.00 to 0.38%, whereas (S)-(+)-citalopram prepared by the prior art process of methanesulfonyl ester derivative contains R-isomer in the range of 0.84 to 1.04%.

What is claimed is:

1. A process for preparation of 1-[3-(dimethylamino)propyl]-1-(4-fluorophenyl)-1,3-dihydro-5-isobenzofuran carbonitrile comprising reacting a compound of formula IVa, in the presence of a base with a compound of formula RX,

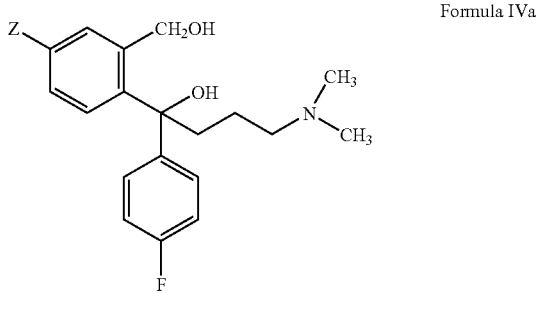

Formula IVa wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl, Z is a cyano group or a group that may be converted to a cyano group; further wherein RX is selected such that an intermediate ether derivative, a compound of formula Va formed from said reaction cyclizes to a compound of formula VI,

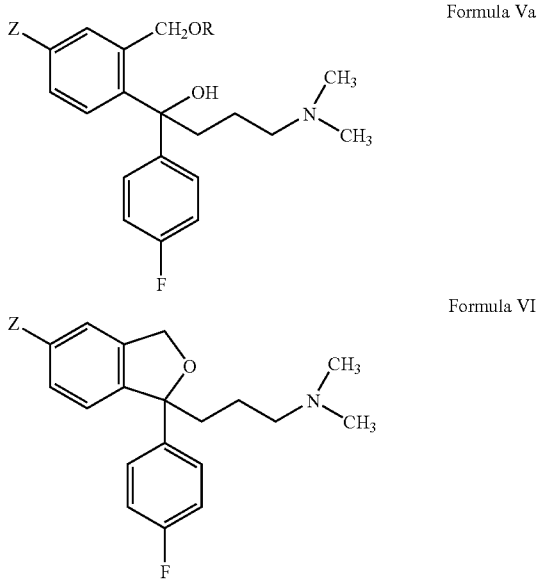

Formula Va

Formula VI and when Z is not a cyano group, conversion of the group Z in the compound of formula VI to a cyano group to form 1-[3-(dimethylamino)propyl]-1-(4-fluorophenyl)-1,3-dihydro-5-isobenzofuran carbonitrile.

2. A process as claimed in claim 1, when Z is a cyano group, and the process comprises reacting 4-[4-(dimethylamino)-1-(4-fluorophenyl)-1-hydroxy-1-butyl]-3-(hydroxylmethyl)-benzonitrile, in the presence of a base, with a compound of formula RX, wherein R is selected from alkyl, alkenyl, aryl and heteroaryl which may be optionally substituted with electron withdrawing groups and X is selected from F, Cl, Br, I, CN, OTf and $OR_1$, wherein Tf represents trifluoromethanesulfonyl group, and $R_1$ is optionally substituted alkyl;

further wherein RX is selected such that an intermediate ether derivative, a compound of formula V formed from said reaction,

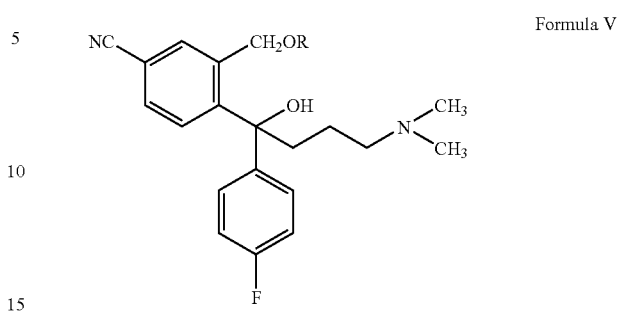

Formula V cyclizes to 1-[3-(dimethylamino)propyl]-1-(4-fluorophenyl)-1,3-dihydro-5-isobenzofuran carbonitrile.)

3. The process as claimed in claim 2 wherein, racemic 1-[3-(dimethylamino)propyl]-1-(4-fluorophenyl)-1,3-dihydro-5-isobenzofuran carbonitrile is formed by reacting racemic 4-[4-(dimethylamino)-1-(4-fluorophenyl)-1-hydroxy-1-butyl]-3-(hydroxymethyl)-benzonitrile with a compound of formula RX.

4. The process as claimed in claim 2 wherein, (S)-(+)-1-[3-(dimethylamino)propyl]-1-(4-fluorophenyl)-1,3-dihydro-5-isobenzofuran carbonitrile is formed by reacting (S)-(−)-4-[4-(dimethylamino)-1-(4-fluorophenyl)-1-hydroxy-1-butyl]-3-(hydroxymethyl)-benzonitrile with a compound of formula RX.

5. The process as claimed in claim 2 wherein, in the compound of the formula RX, the group R is

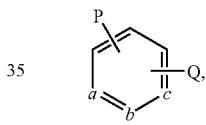

wherein one or more of a, b and c may be carbon or hetero atom which may be same or different, P and Q may be selected from electron withdrawing groups like $NO_2$, $CF_3$, CN, halogen, $COOR_9$, CHO and the like, wherein $R_9$ is alkyl, aryl or heteroaryl.

6. The process as claimed in claim 2 wherein, the compound of formula RX is selected from the group consisting of the following compounds:

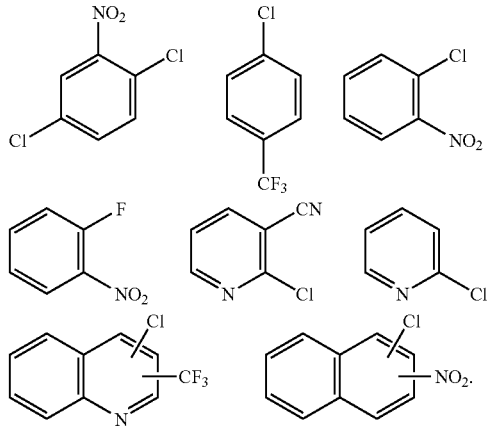

* * * * *